United States Patent
DeRiso et al.

(10) Patent No.: US 9,775,739 B2
(45) Date of Patent: Oct. 3, 2017

(54) SLEEP APNEA PREVENTION

(76) Inventors: Anthony J. DeRiso, Sandusky, OH (US); Albert N. Santilli, Pepper Pike, OH (US)

( * ) Notice: Subject to any disclaimer, the term of this patent is extended or adjusted under 35 U.S.C. 154(b) by 363 days.

(21) Appl. No.: 13/594,625

(22) Filed: Aug. 24, 2012

(65) Prior Publication Data
US 2013/0220340 A1 Aug. 29, 2013

Related U.S. Application Data

(60) Provisional application No. 61/528,115, filed on Aug. 26, 2011.

(51) Int. Cl.
*A61F 5/56* (2006.01)
*A61C 7/06* (2006.01)

(52) U.S. Cl.
CPC . *A61F 5/56* (2013.01); *A61C 7/06* (2013.01)

(58) Field of Classification Search
CPC ........ A61F 5/56; A61F 5/0003; A61F 5/0006; Y10S 602/902; A61C 7/06; A61C 7/065
USPC ..... 128/846, 848, 857, 876, 201.22, 206.21, 128/207.17; 602/17, 902; 27/25.1; 2/421, 171, 171.2; 433/5, 140; 606/201, 606/204.15, 204.25, 204.35; 119/792, 119/814, 821, 831
See application file for complete search history.

(56) References Cited

U.S. PATENT DOCUMENTS

| | | | |
|---|---|---|---|
| 1,587,558 A * | 6/1926 | Sheffield | 128/848 |
| 4,901,737 A | 2/1990 | Toone | |
| 5,092,346 A | 3/1992 | Hays et al. | |
| 5,361,416 A | 11/1994 | Petrie et al. | |
| 5,365,945 A | 11/1994 | Halstrom | |
| 5,427,117 A | 6/1995 | Thornton | |
| 5,462,066 A | 10/1995 | Snyder | |
| 5,566,683 A | 10/1996 | Thornton | |
| 5,570,704 A | 11/1996 | Buzzard et al. | |
| 5,687,743 A | 11/1997 | Goodwin | |
| 5,794,627 A | 8/1998 | Frantz et al. | |
| 5,810,013 A | 9/1998 | Belfer | |
| 5,921,241 A | 7/1999 | Belfer | |
| 6,129,084 A | 10/2000 | Bergersen | |
| 6,918,394 B2 | 7/2005 | Matsuda et al. | |
| 6,981,503 B1 * | 1/2006 | Shapiro | 128/845 |
| 7,174,895 B2 | 2/2007 | Thornton et al. | |
| 7,178,525 B2 * | 2/2007 | Matula et al. | 128/206.27 |
| 7,225,811 B2 | 6/2007 | Ruiz et al. | |

* cited by examiner

Primary Examiner — Keri J Nelson
(74) Attorney, Agent, or Firm — Wayne D. Porter, Jr.

(57) ABSTRACT

A method and apparatus for preventing sleep apnea employs an external clamp that has a first pad that engages the upper lip beneath the nose and a second pad that engages the lower jaw on its underside, behind the mandibular symphysis. The pads are connected to each other by a flexible member, or brace. Preferably the second pad is rounded on that portion that contacts the lower jaw. The clamp is held in place by one or more straps, braces or springs that pass about the patient's head. The first pad is held such that it presses against the upper lip while the second pad closes the lower jaw and pulls it forwardly and upwardly using relatively small forces.

19 Claims, 3 Drawing Sheets

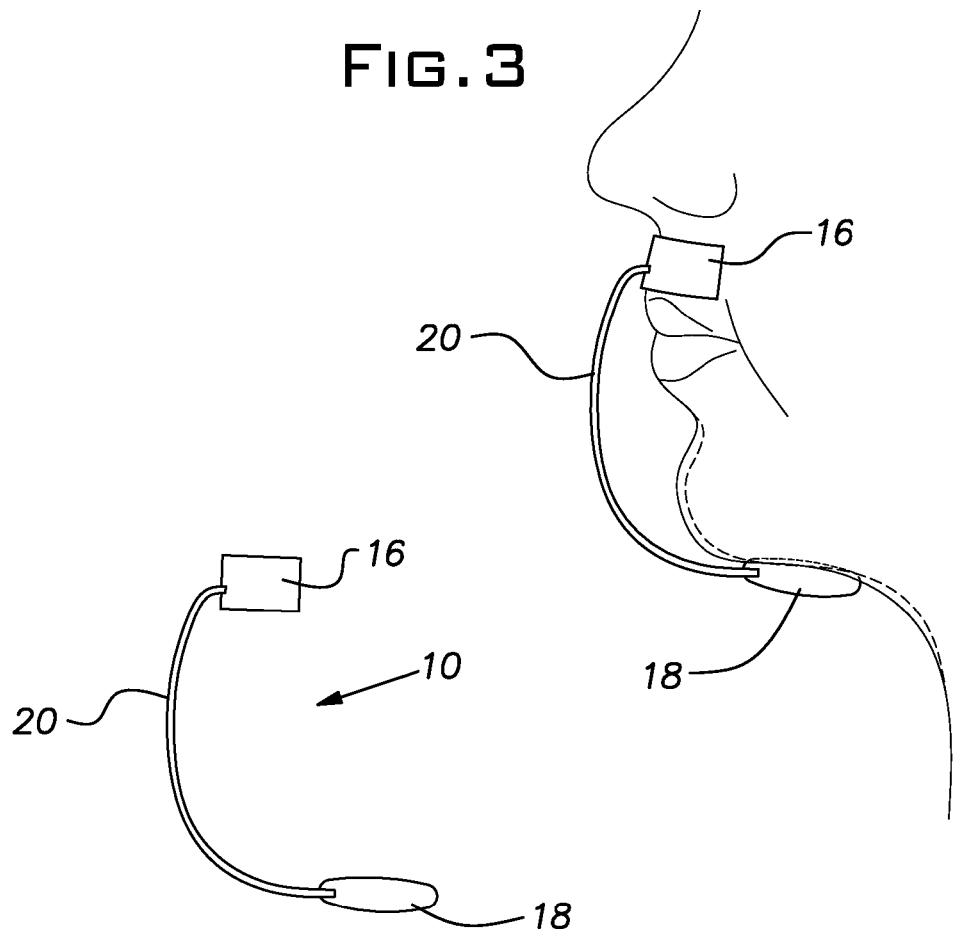
FIG. 3
FIG. 4
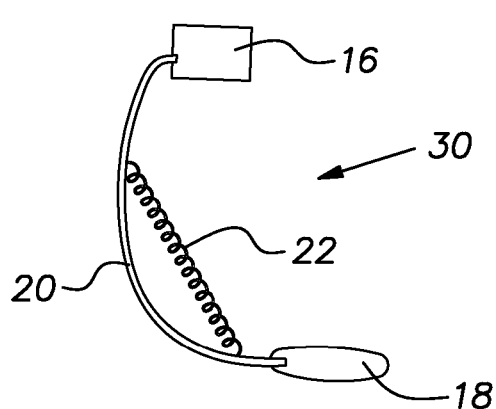
FIG. 5
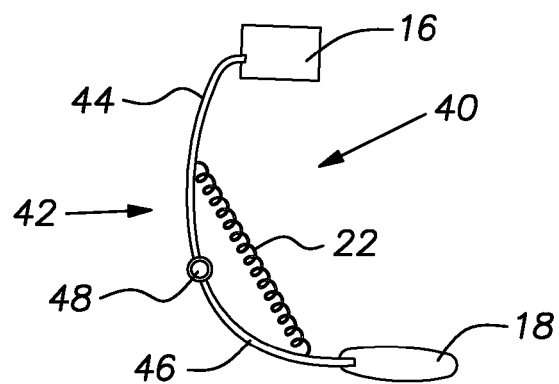
FIG 6

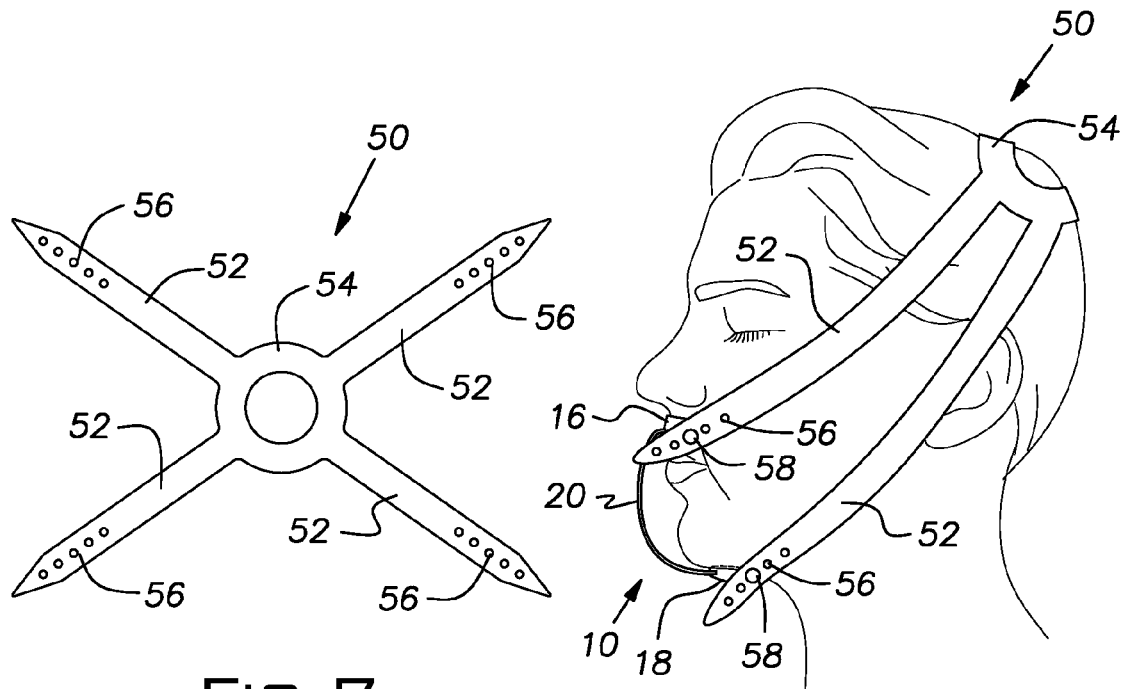
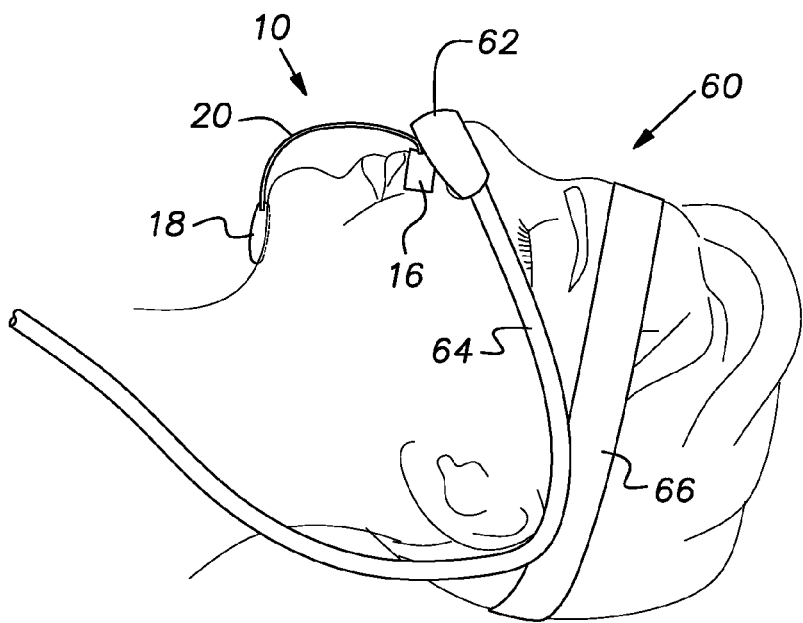

SLEEP APNEA PREVENTION

REFERENCE TO PRIOR APPLICATION

The present application claims priority from provisional application Ser. No. 61/528,115, filed Aug. 26, 2011 by Anthony J. DeRiso II and Albert N. Santilli, entitled Sleep Apnea Prevention, the disclosure of which is incorporated herein by reference.

BACKGROUND OF THE INVENTION

1. Field of the Invention

The present invention relates to the field of preventing snoring and sleep apnea, specifically, obstructive sleep apnea (OSA).

2. Description of the Prior Art

Snoring and sleep apnea are common sleep disorders caused by muscle relaxation and a narrowed pharynx. During sleep, the lower jaw muscles relax and in response the soft palate, uvula, and tongue relax and move to the back of the oral cavity. Consequently, the pharynx narrows. The air passing through a narrowed pharynx may cause the throat to vibrate which causes snoring.

In some people, the pharynx closes so much that enough air can't get through to the lungs. When this happens, the brain sends an alarm to open the airway. Most often, this is associated with a brief arousal from sleep. The brain quickly re-activates the muscles that hold the throat open, air passes through again, and the brain goes back to sleep. The repetitive episodes of complete or partial blockage of breathing are characteristic of obstructive sleep apnea (OSA). According to the American Sleep Apnea Association, more than 12 million Americans suffer from sleep apnea and it is estimated that 10 million remain undiagnosed. If sleep apnea is untreated, it can cause high blood pressure, weight gain, cardiovascular disease, and memory problems to name a few.

There are a variety of treatments to prevent sleep apnea and snoring. Drugs such as muscle relaxants have been used in an attempt to prevent closure of the pharynx during sleep. Masks of various sorts have been used in an attempt to provide gas under positive pressure to the pharynx so that breathing can be maintained. Numerous mechanical approaches also have been attempted. Typically, these involve some sort of dental appliance that is inserted into the mouth and that moves the lower jaw forward relative to the maxilla. By reposition the lower jaw in a forward position, it is believed that the breathing passage will be kept open during sleep, thereby preventing both snoring and sleep apnea.

Mandibular advancement devices, dental appliances or oral mandibular advancement devices, prevent the tongue from blocking the throat and/or advance the lower jaw forward and help keep the airway open during sleep. Other types of treatments range from behavior and lifestyle changes, mechanical therapy, mandibular advancement devices or surgery.

There are several problems with the foregoing approaches. Generally, the use of drugs is undesirable for a number of reasons, including possible dependence on such drugs. Masks with hoses are not well-tolerated and providing a source of pressurized gas can be complex and expensive. With respect to mechanical devices, often it is necessary for a custom-fit appliance to be used, which increases the cost to the patient. Prolonged use of such an applicant also has been reported to permanently change the bite characteristics of the patient.

SUMMARY OF THE INVENTION

The present invention provides a method and apparatus that addresses the foregoing concerns. The apparatus includes an external clamp that has a first pad that engages the upper lip beneath the nose and a second pad that engages the lower jaw on its underside, behind the chin (behind the mandibular symphysis). The pads are connected to each other by a flexible member, or brace. Preferably the second pad is rounded on that portion that contacts the lower jaw. The clamp is held in place by one or more straps, braces or springs. The clamp is held such that it presses against the upper lip while closing the lower jaw and pulling it forwardly and upwardly using relatively small forces.

In alternative embodiments, the brace can be provided with a spring to assist moving the first and second pads toward each other. If desired, the brace can be provided in two segments that are connected by a hinge. The two segments can be connected by a spring in order to assist in moving the first and second pads toward each other.

One of the advantages of the invention is that nothing is disposed within the patient's mouth. Accordingly, nothing contacts the patient's teeth and there is little or no chance that the bite characteristics of the patient will change with prolonged use. Although the clamp and straps need to be adjusted to fit each individual patient, such adjustment should be easy to accomplish by the patient himself. Another advantage is that the patient's mouth is kept closed, thereby requiring breathing through the nose and lessening the chance that snoring will occur. Moreover, the invention is inexpensive to manufacture and avoids the use of an uncomfortable mask covering the patient's face.

BRIEF DESCRIPTION OF THE DRAWINGS

FIG. 3 is another side elevation view of the present invention engaging the patient's upper lip and lower jaw;

FIG. 4 is a side elevation view of a clamp according present invention with straps removed;

FIG. 5 is a view similar to FIG. 4 showing a spring used with a brace included as part of the clamp;

FIG. 6 is a view similar to FIG. 5 showing a hinged or articulated brace and a spring used therewith.

FIG. 7 is a view of a flexible strap that can be used as part of the clamp of the present invention;

FIG. 8 is a view showing the strap of FIG. 7 in use; and

FIG. 9 is a view of the clamp of the present invention being used in conjunction with a breathing mask.

DESCRIPTION OF THE PREFERRED EMBODIMENT

Figure 1:
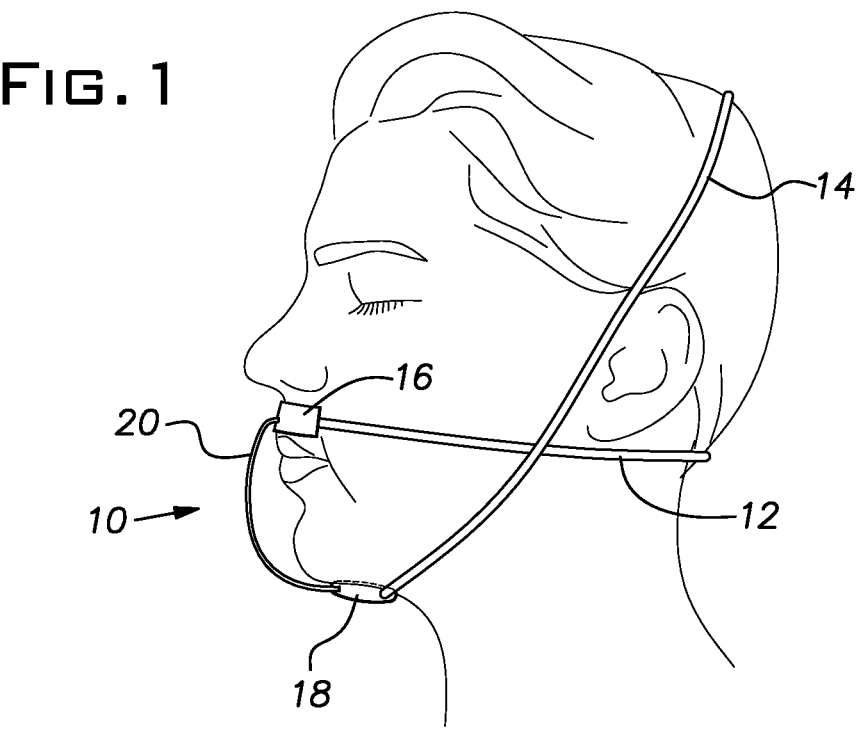
FIG. 1 is a side elevation view of a clamp according to the present invention engaging a patient's upper lip and lower jaw.

The current invention prevents snoring and sleep apnea by engaging a patient's upper lip and engaging the lower jaw on its underside, to gently pull the patient's jaw forwardly and upwardly. Referring to FIG. 1, a clamp 10 according to the current invention is shown. The clamp 10 is held in place on a patient's face by one or more braces, straps 12, 14 and/or springs. The clamp 10 comprises a first pad 16 engaging a patient's upper lip beneath the nose, and a second pad 18 engaging the lower jaw, on its underside. The first pad 16 preferably is rectangular and generally conforms to the size and shape of the patient's upper lip in the region of the nose. The second pad 18 may make contact to the underside of the lower jaw in the area of the anterior triangle, behind the mandibular symphysis. The configuration of the lower jaw in this region is in the nature of a small "hollow" that will receive the pad 18 and which will provide a surface against which force can be applied. Preferably, the second pad 18 is rounded on that portion that contacts the lower jaw.

The first pad 16 is connected to the second pad 18 via a brace 20 or flexible member that extends from the first pad 16, across the mouth, to the second pad 18. The brace 20 is curved to provide a space between the brace 20 and the patient, so the brace 20 does not lie uncomfortably on the patient's face. Preferably, the brace 20 is in the nature of a spring. The force of the brace 20 applied to the first and second pad 16, 18 causes gentle pressure against the upper lip while closing the lower jaw and gently pulling it forwardly and upwardly. This force also keeps the clamp 10 held in place on the patient's face. By pulling the lower jaw forwardly a small amount, the patient's breathing passage can be kept open during sleep. By pulling the lower jaw upwardly a small amount, the patient's mouth can be kept closed during sleep. The force applied by the brace 20 should be the minimum necessary to accomplish the foregoing objectives.

The clamp 10 may have one or more adjustable straps 12, 14 to provide additional support to the clamp 10. The additional support may help keep the clamp 10 in a comfortable position while the patient is sleeping. The straps 12, 14 may be connected to the first pad 16 and/or second pad 18 and extend around the patient's head.

Figure 2:
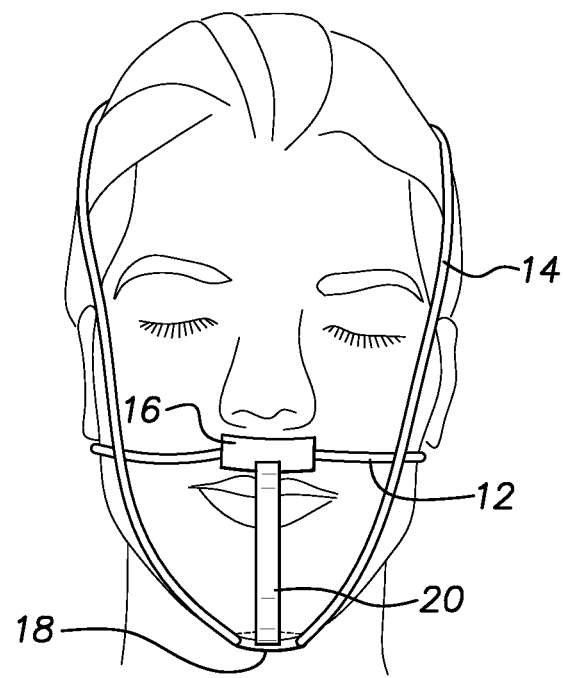
FIG. 2 is a front elevation view of the clamp of FIG. 1 engaging the patient's upper lip and lower jaw.

FIGS. 2-4 show additional views of the current invention. It is to be appreciated that the components of the clamp 10, including the first and second pad 16, 18, brace 20 and straps 12, 14, may be provided in various sizes or may be adjusted by the patient to provide a proper support and fit.

FIG. 5 is a view similar to FIG. 4 showing a second embodiment 30 that is similar to the embodiment 10 and which includes similar elements indicated by like reference numerals. In embodiment 30, a spring 22 is attached to the flexible brace 20 so as to urge the first and second pads 16, 18 toward each other. The positioning of the spring 22 and the strength of the spring 22 can be adjusted to suit the needs of the patient, more particularly to control the amount and direction of force being applied to the upper lip and lower jaw.

FIG. 6 is a view similar to FIG. 4 showing a third embodiment 40 that is similar to the embodiment 10 and which includes similar elements indicated by like reference numerals. In embodiment 40, a brace 42 includes a first segment 44 and a second segment 46 that are connected by a hinge 48. A spring 22 is attached to the segments 44, 46 so as to urge the first and second pads 16, 18 toward each other. The location of the hinge 48, the positioning of the spring 22 and the strength of the spring 22 can be adjusted to suit the needs of the patient, more particularly to control the amount and direction of force being applied to the upper lip and lower jaw.

FIGS. 7 and 8 are views of a flexible strap 50 that can be used to hold the clamps 10, 30, 40 in place. The strap 50 preferably is made of rubber, although it can be made of any suitable flexible material that can conform to the shape of the patient's head. The strap 50 has four legs 52 that radiate outwardly from a ring 54. The legs include a plurality of openings 56 near their ends.

The ring 54 is adapted to fit about the crown of a patient's head. The legs 52 can be pulled about the sides of the patient's head so that pins 58 other projections included as part of the first and second pads 16, 18 can engage selected openings 56 in the legs 52. If the legs 52 and ring 54 are stretched slightly, they will hold the clamps 16, 18 firmly in place. It is believed that the strap 50 may be able to hold the clamps 16, 18 in place more securely than the straps 12, 14.

While the use of ventilators or masks preferably is avoided, nevertheless such accessories can be used with the present invention, if desired or necessary. FIG. 9 shows a fourth embodiment 60 in which the clamp 10 is used (the straps 12, 14 have been omitted for purposes of clarity of illustration). In this embodiment, a ventilator 62 is positioned beneath the patient's nose and is held in place by tubes 64 (only one of which is shown in FIG. 9). A headband 66 is fitted about the patient's head. The tubes 64 are connected to the headband 66. By this construction, air or other fluid can be supplied to the patient's nostrils while the clamp 10 is being used.

It is expected that most or all of the components of the present invention can be made of inexpensive materials such as plastic, rubber, or similar materials. The use of such materials is expected to greatly decrease the cost of the device such that cost will not be a factor in a patient's acquisition of the device. Further, because the device is adjustable by the patient, it is expected that there will be no need to have custom-fit components. The avoidance of the use of custom-fit components is expected to reduce the cost of the device.

Although the present invention has been described in detail, it will be apparent to those skilled in the art that various changes and modifications can be made without departing from the true spirit and scope of the invention as hereinafter claimed. It is intended that all such changes and modifications be encompassed within the scope of the present disclosure and claims.

What is claimed is:

1. A clamp usable for sleep apnea prevention in a patient, comprising:
   a first pad adapted to engage the patient's upper lip adjacent the nose;
   a second pad adapted to contact the underside of the patient's lower jaw in the area of the anterior triangle behind the mandibular symphysis, wherein the second pad is adapted to be received in a small hollow of the patient's jaw and apply force against a surface of the patient's lower jaw;
   a singular, flexible, spring-like brace adapted to be centrally positioned on the first pad and the second pad such that the brace is configured to extend across the patient's mouth, the brace in use applying force to the second pad such that the lower jaw is moved upwardly and forwardly.

2. The clamp of claim 1, further comprising:
   a first strap having first and second ends, the first and second ends of the first strap being connected to the first pad, the first strap passing about the back of the patient's head so as to hold the first pad in place; and
   a second strap having first and second ends, the first and second ends of the second strap being connected to the second pad, the second strap passing about the upper rear portion of the patient's head so as to hold the second pad in place.

3. The clamp of claim 1, further comprising a spring having first and second ends, the first end connected to the brace at a location disposed toward the first pad and the second end connected to the brace at a location disposed toward the second pad, the spring causing the first and second pads to be urged toward each other.

4. The clamp of claim 1, further comprising:
a hinge in the brace located at approximately the midpoint of the brace, the hinge dividing the brace into a first section connected to the first pad and a second section connected to the second pad; and
a spring having first and second ends, the first end of the spring being connected to the first section of the brace and the second end of the spring being connected to the second section of the brace, the spring causing the first and second pads to be urged toward each other.

5. The clamp of claim 1, further comprising a flexible strap in the form of a ring from which four elongate legs extend, the legs having ends and a plurality of openings disposed toward the ends, the openings engaging opposing ends of the first and second pads when the ring is placed upon the crown of the patient's head and the legs are passed along the sides of the patient's head.

6. The clamp of claim 1, further comprising;
a headband adapted to be placed on the patient's head;
a ventilator adapted to be positioned beneath the patient's nostrils; and
tubes connected to the ventilator and attached to the headband, the tubes permitting air or other fluid to be supplied to the ventilator.

7. The clamp of claim 1, wherein the first pad is rectangular and generally conforms to the size and shape of the patient's upper lip in the region of the nose.

8. The clamp of claim 1, wherein the second pad is rounded and generally conforms to the size and shape of the patient's lower jaw in the region of the lower jaw behind the mandibular symphysis.

9. The clamp of claim 1, wherein the first and second pads and the brace are made of a plastics material.

10. A method for preventing sleep apnea in a patient, comprising:
providing a first pad;
providing a second pad;
providing a singular, flexible, spring-like brace that extends between and connects the first and second pads, the brace in use being positioned centrally on the first pad and the second pad such that the brace is configured to extend across the patient's mouth;
placing the first pad against the patient's upper lip adjacent the nose;
placing the second pad against the underside of the patient's lower jaw in the area of the anterior triangle behind the mandibular symphysis, wherein the second pad is adapted to be received in a small hollow of the patient's lower jaw and apply force against a surface of the patient's lower jaw; and
applying force to the lower jaw through the second pad such that the lower jaw is moved upwardly and forwardly.

11. The method of claim 10, wherein the first and second pads are held in place by straps that pass about the patient's head.

12. The method of claim 10, further comprising the steps of:
providing a spring having first and second ends; and
connecting the first and second ends of the spring to the brace, the spring urging the first and second pads toward each other.

13. The method of claim 10, further comprising the steps of:
providing a hinge in the region of the midpoint of the brace so as to divide the brace into first and second sections;
providing a spring having first and second ends; and
connecting the first end of the spring to the first section of the brace; and
connecting the second end of the spring to the second section of the brace, the spring urging the first and second pads toward each other.

14. A clamp usable for sleep apnea prevention in a patient, comprising:
a first pad adapted to engage the patient's upper lip adjacent the nose;
a second pad adapted to engage the patient's lower jaw behind the mandibular symphysis;
a brace extending between and connecting the first and second pads, the brace in use applying force to the second pad such that the lower jaw is moved upwardly and forwardly;
a hinge in the brace located at approximately the midpoint of the brace, the hinge dividing the brace into a first section connected to the first pad and a second section connected to the second pad; and
a spring having first and second ends, the first end of the spring being connected to the first section of the brace and the second end of the spring being connected to the second section of the brace, the spring causing the first and second pads to be urged toward each other.

15. The clamp of claim 14, wherein the first pad is rectangular and generally conforms to the size and shape of the patient's upper lip in the region of the nose.

16. The clamp of claim 14, wherein the second pad is rounded and generally conforms to the size and shape of the patient's lower jaw in the region of the lower jaw behind the mandibular symphysis.

17. A method for preventing sleep apnea in a patient, comprising:
providing a first pad;
providing a second pad;
providing a brace that extends between and connects the first and second pads;
placing the first pad against the patient's upper lip adjacent the nose;
placing the second pad against the patient's lower jaw behind the mandibular symphysis;
applying force to the lower jaw through the second pad such that the lower jaw is moved upwardly and forwardly;
providing a hinge in the region of the midpoint of the brace so as to divide the brace into first and second sections;
providing a spring having first and second ends;
connecting the first end of the spring to the first section of the brace; and
connecting the second end of the spring to the second section of the brace, the spring urging the first and second pads toward each other.

18. The method of claim 17 wherein the first pad is rectangular and generally conforms to the size and shape of the patient's upper lip in the region of the nose.

19. The method of claim 17, wherein the second pad is rounded and generally conforms to the size and shape of the patient's lower jaw in the region of the lower jaw behind the mandibular symphysis.

* * * * *